United States Patent
Drndic et al.

(10) Patent No.: US 11,338,247 B2
(45) Date of Patent: May 24, 2022

(54) METHOD OF STEM-BASED DRILLING OF ULTRATHIN SILICON NITRIDE NANOPORES AND NANOPORE ARRAYS

(71) Applicant: The Trustees of The University of Pennsylvania, Philadelphia, PA (US)

(72) Inventors: Marija Drndic, Philadelphia, PA (US); Julio A. Rodriguez-Manzo, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 403 days.

(21) Appl. No.: 15/511,829

(22) PCT Filed: Sep. 17, 2015

(86) PCT No.: PCT/US2015/050603
§ 371 (c)(1),
(2) Date: Mar. 16, 2017

(87) PCT Pub. No.: WO2016/044536
PCT Pub. Date: Mar. 24, 2016

(65) Prior Publication Data
US 2017/0304777 A1    Oct. 26, 2017

Related U.S. Application Data

(60) Provisional application No. 62/051,987, filed on Sep. 18, 2014.

(51) Int. Cl.
*B01D 67/00* (2006.01)
*G01N 33/487* (2006.01)
(Continued)

(52) U.S. Cl.
CPC .......... *B01D 67/006* (2013.01); *B01D 71/02* (2013.01); *C12Q 1/6869* (2013.01);
(Continued)

(58) Field of Classification Search
CPC .. B01D 67/006; B01D 71/02; B01D 2325/04; B01D 2325/02; H01J 37/31;
(Continued)

(56) References Cited

U.S. PATENT DOCUMENTS

| 2010/0009134 A1 | 1/2010 | Drndic et al. |
| 2011/0226623 A1* | 9/2011 | Timp .................. C12Q 1/6869 |
| | | 204/543 |

(Continued)

FOREIGN PATENT DOCUMENTS

| WO | WO 2014/052616 A2 | 4/2014 |
| WO | WO 2014/153047 A1 | 9/2014 |

(Continued)

OTHER PUBLICATIONS

Liebes et al. (Y Liebes, B Hadad, N Ashkenasy, Effects of electrons on the shape of nanopores prepared by focused electron beam induced etching, Nanotechnology 22 (2011) 285303) (Year: 2011).*

(Continued)

*Primary Examiner* — Joshua L Allen
(74) *Attorney, Agent, or Firm* — BakerHostetler LLP (57) ABSTRACT

The invention concerns methods for preparing a nanoporous silicon nitride membrane comprising (i) ablating portions of at least one side of the membrane with an electron beam to reduce the thickness of the portions to between about 0.5 and 5 nanometers, and (ii) penetrating subportions of the ablated portions of the membrane with an electron beam to form nanopores having internal surfaces which are predominantly silicon rich compared to unablated portions of the membrane.

29 Claims, 8 Drawing Sheets (51) Int. Cl.
  *B01D 71/02*    (2006.01)
  *H01J 37/317*   (2006.01)
  *H01J 37/31*    (2006.01)
  *C12Q 1/6869*   (2018.01)
  *G01N 27/447*   (2006.01)
  *H01J 37/305*   (2006.01)

(52) U.S. Cl.
  CPC .  *G01N 27/44791* (2013.01); *G01N 33/48721* (2013.01); *H01J 37/3056* (2013.01); *H01J 37/31* (2013.01); *H01J 37/317* (2013.01); *B01D 2325/02* (2013.01); *B01D 2325/04* (2013.01); *H01J 2237/3118* (2013.01)

(58) Field of Classification Search
  CPC .............. H01J 37/317; H01J 37/3056; H01J 2237/3118; G01N 27/44791; G01N 33/48721; C12Q 1/6869
  See application file for complete search history.

(56) References Cited

U.S. PATENT DOCUMENTS

| | | | |
|---|---|---|---|
| 2013/0092541 A1* | 4/2013 | Drndic | G01N 27/44791 204/543 |
| 2013/0309776 A1 | 11/2013 | Drndic et al. | |
| 2016/0033471 A1* | 2/2016 | Meller | G01N 33/48721 435/6.1 |

FOREIGN PATENT DOCUMENTS

| WO | WO-2014153047 A1 * | 9/2014 | ............ G01N 27/49 |
|---|---|---|---|
| WO | WO 2014/165372 A1 | 10/2014 | |

OTHER PUBLICATIONS

Kim et al. (MJ Kim, M Wanunu, DC Bell, A Meller, Rapid fabrication of uniformly sized nanopores and nanopore arrays for parallel DNA analysis, Adv. Mater. 18 (2006) 3149-3153) (Year: 2006).*

Fologea et al. (D Fologea, M Gershow, B Ledden, DS McNabb, JA Golovchenko, J Li, Detecting single stranded DNA with a solid state nanopore, Nano Letters 5(10) (2005) 1905-1909) (Year: 2005).*

Rosenstein et al. (JK Rosenstein, M Wanunu, CA Merchant, M Drndic KL Shepard, Integrated nanopore sensing platform with sub-microsecond temporal resolution, Nat Methods 9(5) 2012 487-492) (Year: 2012).*

Wu et al. (M-Y Wu, D Krapf, M Zandbergen, H Zandbergen, Formation of nanopores in a SiN/SiO2 membrane with an electron beam, Appl. Phys. Lett. 87 (2005) 113106) (Year: 2005).*

Assad et al. (ON Assad, ND Fiori, AH Squires, A Meller, Two color DNA barcode detection in photoluminescence suppressed silicon nitride nanopores, Nano Lett. 15 (2015) 745-752) (Year: 2015).*

Carlsen et al. (AT Carlsen, QK Zahid, J Ruzicka, EW Taylor, AD Hall, Interpreting the conductance blockades of DNA translocations through solid-state nanopores, ACS Nano 8(5) (2014) 4754-4760) (Year: 2014).*

Fiori et al. (ND Fiori, A Squires, D Bar, T Gilboa, TD Moustakas, A Meller, Optoelectronic control of surface charge and translocation dynamics in solid-state nanopores, Nat. Nanotechnol. 8(12) (2013) 946-951) (Year: 2013).*

George et al. (HB George, Y Tang, X Chen, J Li, JW Hutchinson, JA Golovchenko, MJ Aziz, Nanopore fabrication in amorphous Si: Viscous flow model and comparison to experiment, J. Appl. Phys. 108 (2010) 014310) (Year: 2010).*

Howitt et al. (DG Howitt, SJ Chen, BC Gierhart, RL Smith, SD Collins, The electron beam hole drilling of silicon nitride thin films, J. Appl. Phys. 103 (2008) 024310) (Year: 2008).*

Kudr et al., "Fabrication of solid-state nanopores and its perspectives", Electrophoresis, 2015, vol. 36, No. 19, 1-13.

Liebes et al., "Effects of electrons on the shape of nanopores prepared by foucused electron beam induced etching", Nanotechnology, 2011, vol. 22, No. 28, 285303, 9 pages.

Wu et al., "Surface Modification of Ceramic Materials Using Excimer Laser", Journal of Materials & Science Technology, 2000, vol. 16, No. 4, 401-404.

* cited by examiner

METHOD OF STEM-BASED DRILLING OF ULTRATHIN SILICON NITRIDE NANOPORES AND NANOPORE ARRAYS

CROSS-REFERENCE TO RELATED APPLICATIONS

This application is the National Stage Application of International Patent Application No. PCT/US2015/050603, filed Sep. 17, 2015, which claims the benefit of U.S. Patent Application No. 62/051,987 filed on Sep. 18, 2014, the disclosure of which are incorporated herein by reference in its entirety.

GOVERNMENT RIGHTS

This invention was made with government support under grants HG004767 and HG006879 awarded by the National Institutes of Health (NIH). The government has certain rights in the invention.

TECHNICAL FIELD

The invention concerns inter alia concerns methods of forming pores in silicon nitride membranes.

BACKGROUND

Nanopores in synthetic membranes hold great promise as platforms for next generation DNA sequencing, as well as for other applications in genomics. Solid-state nanopores have been playing a major role for realizing these efforts, as they exhibit reproducible structure, scale-up capabilities, stability, and robustness. Low-stress silicon nitride (SiN), silicon oxide, and aluminum oxide have been used as membranes for the fabrication of solid-state nanopores.

Nanopore-based applications rely on reading the ion current of an electrolyte through the nanopore as biomolecules are threaded through the pore. The ion current highly depends on voltage, salt concentration, temperature, and the pore geometry. Analogous to the sharpness of an AFM tip, the length of the nanopore determines the overall resolution of the nanopore technique.

The reported thickness values of solid-state nanopores lie in the range of 20-50 nm, which provides a maximum readout resolution for double-stranded DNA of around 60-150 basepairs. This resolution, however, hinders the quality of information that is recovered from ion-current signals. Fabrication of thinner membranes, however, poses its own challenges, and is limited by physical stability, resulting in cracks and holes through the membrane that render the devices unusable. In light of the demand for a cheaper DNA sequencing, genomic analysis, RNA analysis, protein analysis, and other methods for ultrasensitive molecular analysis, there is a need in the art for ultrathin (e.g., <10 nm) solid-state membrane substrates for nanopore analysis, and for related methods of fabricating and of using such devices.

SUMMARY

In some aspects, the invention concerns methods for preparing a nanoporous silicon nitride ($SiN_x$) membrane comprising
 ablating portions of at least one side of the membrane with an electron beam to reduce the thickness of the portions to between about 0.5 and 5 nanometers;
 penetrating subportions of the ablated portions of the membrane with an electron beam to form nanopores having internal surfaces which are predominantly silicon rich compared to unablated portions of the membrane.

In certain embodiments, each of said portions comprises one nanopore.

While any suitable shaped nanopore may be utilized, some nanopores have an hourglass shape. In other embodiments, the nanopore is a cylindrical shape.

In some embodiments, the nanopores have a cross-section of less than or equal to about 1 nm at its widest point. In other embodiments, the nanopores have a cross-section of less than or equal to about 0.5 nm at its widest point. In some preferred embodiments, the pore cross-sectional diameter is in the range of 1 to ⅓ (½ to ⅓ in some embodiments) of the thickness of the ablated portion. In certain embodiments, the diameter/thickness of the pore is 1-2 nm range/0.5 to 2 nm range ideal (especially for DNA sequencing. The membrane can be ~0.3 nm-0.6 nm thick. In some preferred embodiments, the nanopore diameter should be 1-1.5 nm for single stranded DNA and 2 to 2.5 nm for double stranded DNA.

Any suitable laser may be used to ablate portions of the membrane. In some preferred embodiments, however, the electron beam is a scanning transmission electron beam is a condensed electron beam of a transmission electron microscope (TEM) operated in scanning transmission electron (STEM) mode. In some embodiments, the beam is operated at 200 kV, 100-300 kV in some embodiments, 150-250 kV in certain embodiments, 180-220 kV in some embodiments.

The thickness of the portion is controlled utilizing measurements of current density during ablating. By monitoring current density, where density is higher indicates that more electrons go through and the section is thinner. Where current density is lower, this means the section is thicker. As such, one can monitor current density and where it is really high that means this is the thinnest region and we can drill there. In some embodiments, a map of current density numbers across the membrane is produced and we can drill at points with highest current density.

Prior to ablating, the membrane typically has a thickness in the range of from about 20 nm to about 100 nm prior to contact with the electron beam. After ablating, the preselected portion has a thickness of 0.5-2 nm, or 2-5 nm in some embodiments, or in certain embodiments, 2-4 nm.

Typically, the nanopores are within 1 nm or the center of the ablated portion. In some preferred embodiments, the nanopore is in the center of the ablated portion.

While any suitable geometry may be utilized, typically the preselected portions are a square or rectangle typically having each dimension being in the range of about 10-30 nm. In one preferred embodiment, the preselected portion has a 20 nm×20 nm in surface area on the membrane.

In another aspect, the invention concerns macromolecule analysis components comprising a membrane described herein.

In yet another aspect, the invention concerns methods of sequencing DNA or RNA sequences using an instrument having a macromolecule analysis component described herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale or proportion. In the drawings:

FIGS. 1A-1F illustrate fabrication and characterization of thin membranes in free-standing $SiN_x$ films.

FIGS. 2A-2D provide a schematic illustration of alpha-hemolysine, $SiN_x$, MspA and graphene nanopores. In this picture, all nanopores have 1.2 nm diameters. The $SiN_x$ pore in this image has a membrane thickness of 5 nm and effective thickness about 1.7 nm. The STEM-based method developed here can further reduce the thickness of $SiN_x$ membranes down to dimensions similar to the MspA pore.

FIGS. 6A-6F illustrate STEM fabrication of nanopores. Electron beam convergence angle and exposure dose effects on irradiation-induced pore formation in 42 nm-thick $SiN_x$ films, for a fixed electron beam diameter D=2.4 nm. In FIG. 6F the right y axis indicates the film thickness at the pores as a function of the exposure time. The exposure dose is proportional to the exposure time.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "approximately" or "about," it will be understood that the particular value forms another embodiment. All ranges are inclusive and combinable, and all publications cited herein are incorporated by reference in their entireties for any and all purposes.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. Documents mentioned herein are incorporated in their entireties for any and all purposes.

In one aspect, the invention concerns methods for preparing a nanoporous silicon nitride membrane comprising (i) ablating portions of at least one side of the membrane with an electron beam to reduce the thickness of the portions to between about 2 and 5 nanometers, and (ii) penetrating subportions of the ablated portions of the membrane with an electron beam to form nanopores having internal surfaces which are predominantly silicon rich compared to unablated portions of the membrane.

In another aspect, the invention concerns macromolecule analysis components that comprise a membrane described herein. Some detection devices include a first capture material configured to bind preferentially to a first molecule; a membrane having a thickness in the range of from about 20 nm to about 100 nm, and the membrane having a thinned region, the thinned region having a thickness in the range of from about 0.1 nm to about 20 nm, and a first pore extending through the thinned region, the first pore being in fluid communication with the capture material; and a detector configured to detect a signal related to passage of the first molecule through the first pore. Certain devices are described in published U.S. Patent Application Nos. 2013-0092541 and 2013-0309776, and in published PCT Patent Application No. WO 2014/052616, the disclosures of which are incorporated herein by reference. The devices may be used to detect DNA, RNA, tRNA, mRNA, and the like.

In yet another aspect, the invention concerns methods of sequencing DNA, RNA, tRNA, mRNA, and the like by using an instrument having a macromolecule analysis component described herein. Some methods of detecting an analyte include contacting a sample to a first capture material that preferentially binds to a first analyte; eluting the first analyte from the capture material; translocating the first analyte through a first pore disposed in a thinned region of a membrane, the thinned region having a thickness in the range of from about 0.1 nm to about 20 nm; and detecting a signal related to the translocation of the molecule through the first pore. Certain methods are described in published U.S. Patent Application Nos. 2013-0092541 and 2013-0309776, and in published PCT Patent Application No. WO 2014/052616, the disclosures of which are incorporated herein by reference.

Figure 1A:
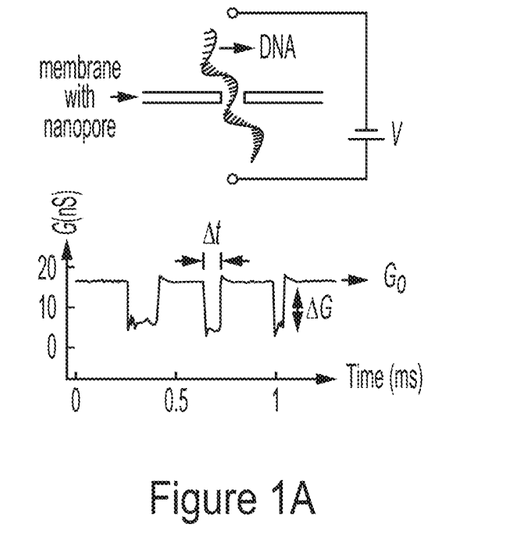
FIG. 1A provides a diagram of a $SiN_x$ film containing a thinned area and a nanopore. After interacting with the film the electron beam is collected with HAADF STEM and electron energy loss spectroscopy (EELS) detectors.
Figure 1B:
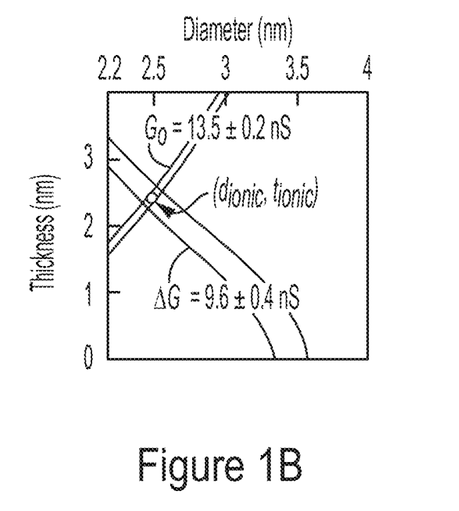
FIG. 1B provides HAADF STEM images before (left) and after (right) a thin area of 56×56 nm$^2$ was created in a $SiN_x$ film. Line profiles (as the one indicated by the dashed line) from HAADF STEM images acquired from areas of a $SiN_x$ film irradiated with eight different electron doses show how the HAADF signal decreases for decreasing membrane thicknesses (bottom). The HAADF signals for the initial and final thickness (0 nm) are indicated by ti and tf, respectively.

Nanopores made on solid-state membranes can detect the translocation of individual charged molecules in salt solution when an ionic current ($\Delta I_{ionic}$) is induced through the nanopore by applying an electrical potential (V) to the solution (FIG. 1A). A molecule like DNA passing through the nanopore blocks ions producing an ionic current blockage ($\Delta I_{ionic}$). This technique is being investigated as a platform to sequence DNA. The thickness of the membrane surrounding the nanopore defines in part the quality of the detection (signal-to-noise ratio). The conductance of ion flow through a nanopore can be expressed as:

$$\frac{Go}{\sigma} = \left(\frac{4t}{\pi d^2} + \frac{1}{d}\right)^{-1}$$

where t is the effective thickness of the membrane, d the effective diameter of the nanopore. For translocating DNA molecules $\Delta I_{ionic}$ can be expressed in the simplest model as the difference between the ion current through an empty pore and the ion current through a DNA-occluded pore:

$$\frac{\Delta I_{ionic}}{V \times \sigma} = \frac{\Delta G_{ionic}}{\sigma} = \left(\frac{4t}{\pi d^2} + \frac{1}{d}\right)^{-1} - \left(\frac{4t}{\pi(d^2 - dDNA2)} + \frac{1}{Sqrt(d^2 - dDNA2)}\right)^{-1}$$

where dDNA is the diameter of the DNA molecule. From these two equations and the measured values of Go and $\Delta G$, the parameters d and t can be calculated (FIG. 1B).

For t=0, the maximum values of $\Delta G$ depend on d as $\Delta G_{max}(d) = [d - sqrt(d^2 - d^2 DNA)] \times \sigma$, where smaller diameters correspond to larger $\Delta G$. The maximum $\Delta G_{max}$ is achieved with the smallest diameter of d=dDNA and t=0. Assuming ddsDNA=2.2 nm and dssDNA=1.1 nm, $\Delta G_{dsDNA,max}$=2.2 nm×σ for d=2.2 nm and $\Delta G_{ssDNA,max}$=1.1 nm×σ for d=1.1 nm. In 1M KCl solution, these values are $\Delta G_{dsDNA,max}$=24 nS and $\Delta G_{ssDNA,max}$=12 nS.

Efforts to fabricate thin membranes for nanopores include thinning of $SiN_x$ films with reactive ion etching or a focused Helium beam, and the use of thin materials such as graphene, boron nitride, hafnium oxide and molybdenum disulfide.

Measurements of open pore conductance and conductance reductions during DNA translocations are reliable indicators of the effective insulating nanopore thickness in ion solution. In particular, higher conductances correspond to lower effective thicknesses of nanopores. Regardless of the choice of theoretical frameworks used to interpret the DNA translocation data, a comparison of measured normalized signal conductances is a robust metric that can be used to compare the effective thicknesses of nanopores in different materials. We use the measured signal conductance as the most reliable indicator of the effective thickness.

Figure 1C:
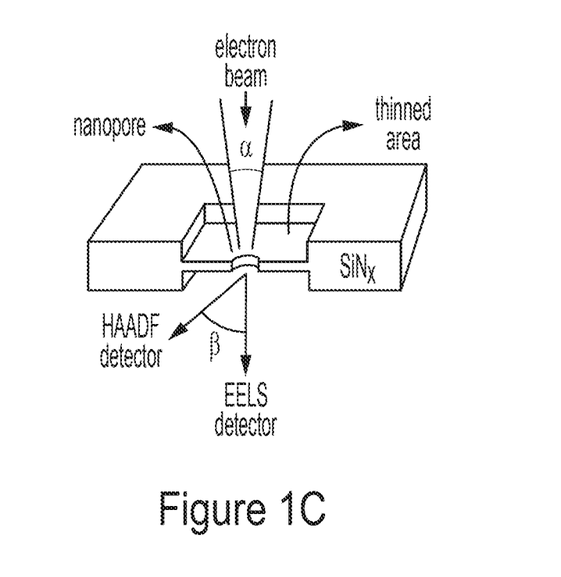
FIG. 1C provides EELS spectra taken from the areas of the $SiN_x$ film thinned with eight different electron doses show how the EELS intensity drops and the N K-shell ionization edge fades in the thinned areas. The Si $L_{23}$ and N K-edges are located at 100 and 400 eV, respectively, in the EELS spectrum. The inset shows the fading of the N K-edge.

Thin membranes were fabricated from free-standing $SiN_x$ films (with thicknesses~50 nm) with the condensed electron beam of a TEM operated in STEM mode at 200 kV. For thinning, the beam was scanned over an area of the $SiN_x$ film while an HAADF STEM image and an EELS spectrum were acquired continuously and simultaneously, as depicted in FIG. 1C. Irradiation with a 200 keV-beam causes sputtering of N and Si atoms and, in our experiments, this loss of mass was observed and quantified as a drop in the intensities of the HAADF STEM image and the EELS spectrum. The sputtering rate is faster for N than for Si. Thus, the irradiation process resulted in thinned membranes of mostly amorphous silicon (a-Si).

Figure 1D:
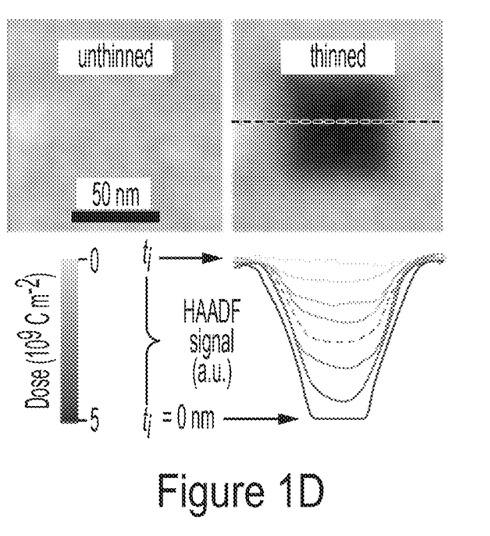
FIG. 1D provides normalized EELS Si L (dark gray) and N K-edge (light gray) signals as a func-tion of electron dose (or thinning) of the EELS spectra shown in FIG. 1B. The top axis indicates the ratio of N to Si atoms for each thinning step. The right axis shows the EELS-estimated $t_f/t_i$ ratio for cases in which the N K-edge signal drops more than 70% (indicated by the dashed line) of the initial value. In this example, the thinnest membrane corresponds to 13% of the initial thickness.

HAADF STEM images of a $SiN_x$ film area before and after electron irradiation are shown in FIG. 1D. In this example, a 2.4 nm diameter beam with a current density of 1.2×109 A m$^{-2}$ was scanned continuously over a 256×256 grid covering 42×42 nm$^2$ for a total electron dose (total charge deposited per unit area) of 3.8×109 C m$^{-2}$. For each scan the beam dwell time per grid point (or pixel in the HAADF STEM image) was set to 20 μs.

The HAADF signal is proportional to the mass content of the imaged area if the electrons traversing the $SiN_x$ film are scattered only once (a reasonable assumption for thicknesses<50 nm). Therefore, the thinning process can be qualitatively correlated with the HAADF image that is acquired at the same time, as shown in the bottom part of FIG. 1D. EELS taken at different thinning doses show that irradiation causes a drop in the EEL background intensity, a downward shift of 5 eV of the Si $L_{23}$-shell ionization edge maximum (from 106 to 101 eV) and the fading of the N K-edge at 400 eV. These signatures indicate loss of mass and a significant depletion of N.

Figure 1E:
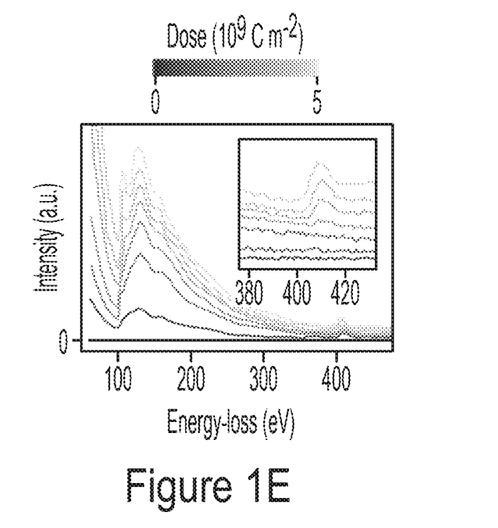

The continuous acquisition of the EEL signal (refresh<0.1 s) during irradiation allows to control the membrane final thickness because the intensity of each of the ionization edges is pro-portional to the number of atoms under the beam, 14 which in turn is proportional to the mem-brane thickness (mass=thickness×area×ρ, where ρ is the density). FIG. 1E shows the nor-malized EEL signal of the Si L and N K-edges as a function of electron dose during a thinning process where a 1.9 nm diameter beam, with a current density of 4.5×109 A m$^{-2}$, and the same scanning conditions described above were used. For each electron dose we quantified the ratio of N to Si atoms 14 and the top axis of FIG. 1E enumerates the results. The ratio approximates the expected value for $Si_3N_4$ (N:Si=1.3) at the beginning of the thinning process and diminishes down to 0.1 for the highest electron dose, indicating a drop of more than 90% in the content of N with respect to Si in the membrane.

Figure 1F:
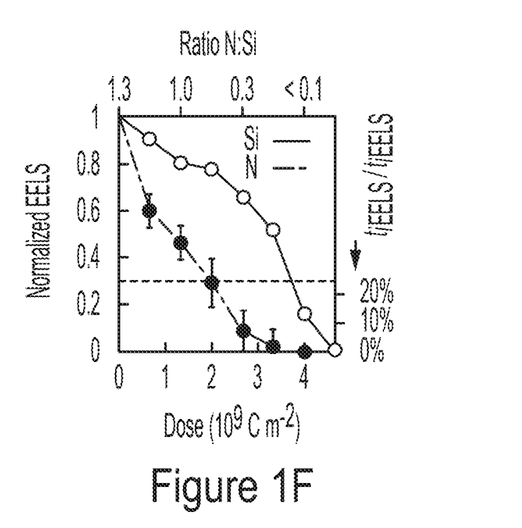

Based on the EEL signal the final thickness ($t_f$) of the thinned membrane can be expressed as:

$$t_f = t_i \times \frac{I_{Si_f}}{I_{Si_i}} \times \frac{\rho_{Si_3N_4}}{\rho_{a-Si}}$$

where $t_i$ is the initial thickness of the silicon nitride film, $ISi_f$ and $ISi_i$ are the Si L-edge signals for the thinned and unthinned membranes, and $\rho Si_3N_4$ and $\rho a$-Si are the densities of $Si_3N_4$ and a-Si. Membranes showing a drop of more than 70% of the initial Si L-edge signal are expected to have a ratio of N to Si atoms of less than 10%, and only this type of membrane were included in our EELS-based estimation of the thickness to take into account the change in mass density (as indicated by the dashed line FIG. 1F).

To compare the performance of these nanopores with different thicknesses (and with published work) we choose the average $\Delta I$ per unit of V. The thickness of some films has been push to the limit and Table summarizes values for average $\Delta I$ per volt. To our knowledge, the best values are in the order of 5-10 nS normalized at 1 M KCl for dsDNA.

Based on TEM imaging, ion conductance measurements, and annular-dark field scanning TEM (ADF-STEM) studies, $SiN_x$ nanopore shapes are known to deviate from a perfect cylinder. Electron tomography shows that $SiN_x$ nanopores membranes have a truncated double-cone or "hourglass" structure. Nevertheless, a simplified geometric model using an equivalent cylinder of reduced effective thickness ($h_{eff}$) is sufficient to quantitatively explain the open and blocked current values measured during DNA translocations. By fitting both the ionic open-pore and blocked-pore current data for many different-diameter nanopores with the same membrane thickness, $h_{eff}$ is estimated to be one-third of the actual membrane thickness (h). This implies that TEM drilled nanopores in 5-nm-thick $SiN_x$ membranes have $h_{eff}$~1.7 nm. To make a $SiN_x$ effective constriction as thin as the constriction in MspA, a nanopore would need to be drilled through a 1.5-nm-thick $SiN_x$ membrane, giving $h_{eff}$~0.5 nm, which roughly spans four DNA bases.

We have made and measured nanopores in graphene, boron nitride, and other two-dimensional materials, but we chose to proceed with thinned $SiN_x$ for sequencing as these pores consistently show the best results in terms of yield of pores allowing translocations and the signal to noise ratio. This conclusion is also supported by the current literature,

TABLE 1

Figure 2A:
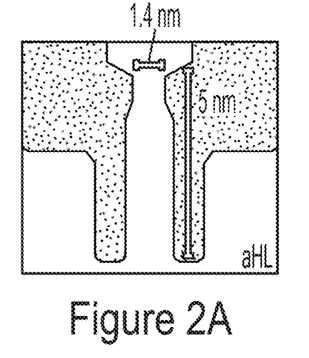
Figure 2B:
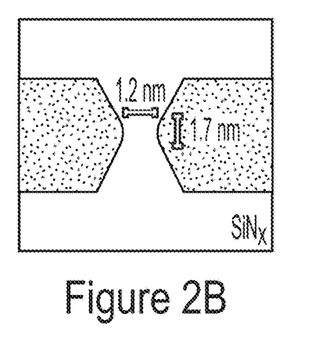
Figure 2C:
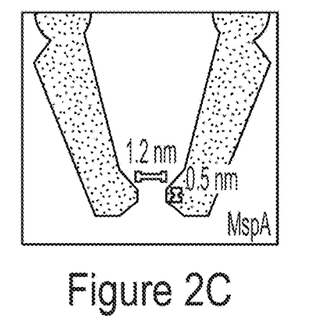
Figure 3:
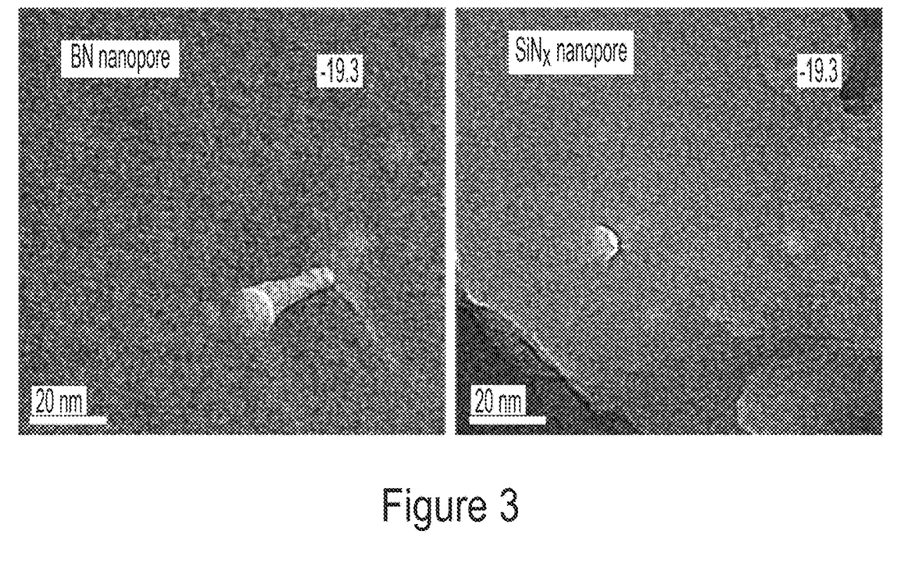
FIG. 3. TEM images showing the 3D profile of nanopores, obtained by tilting the TEM stage by ~−20 degrees. These images show half of the nanopore (the other, symmetric half is obtained from tilting the TEM stage by +20 degrees, and is not shown here).
Figure 4:
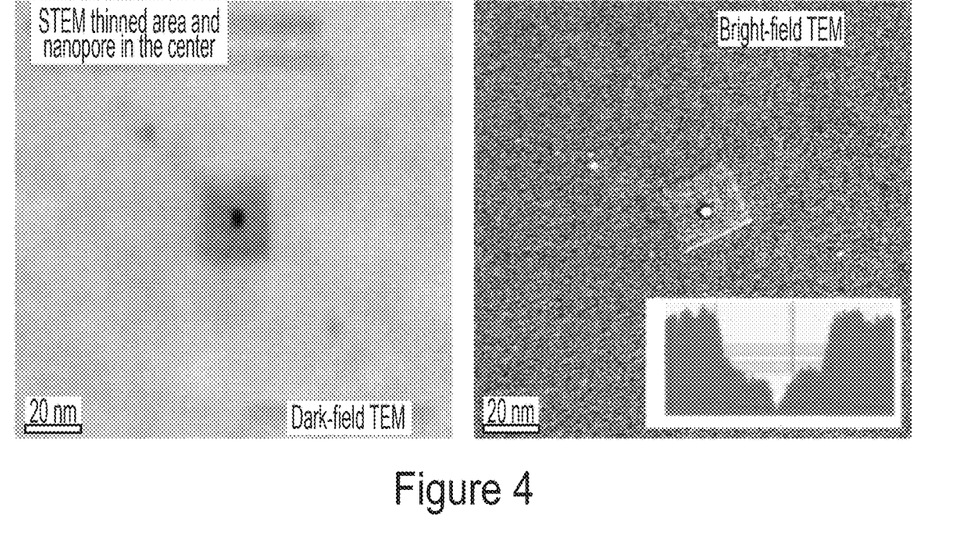
FIG. 4: Dark and bright field TEM images showing a 20×20 nm square area where the $SiN_x$ membrane was thinned with the STEM beam. The inset shows the mass profile of the thinned area and the nanopore in the middle.
Figure 5:
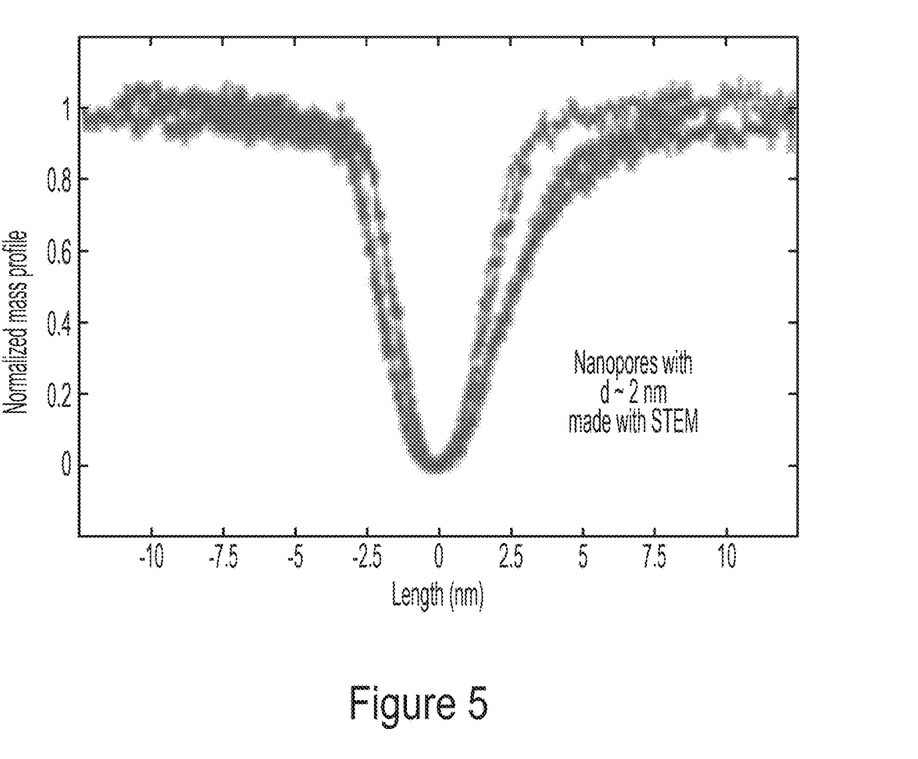
FIG. 5: Mass profile of several STEM-drilled, ~2 nm diameter $SiN_x$ pores to study the size reproducibility.

| Paper | $\Delta I_{ionic}$ (nA) | V (mV) | $\Delta G_{ionic}$ (nS) | Material | $\phi$ (nm) | t (nm) | DNA | Sol. | $\sigma$ (S m$^{-2}$) |
|---|---|---|---|---|---|---|---|---|---|
| [2]FIG. 3d | 3.7 | 300 | 12.3 | $SiN_x$ | 4 | 2.6* | ds 3 kbp | 1M KCl | 13.7* |
| [3]FIG. 4 | 4.2-5.1 | 1000 | 4.2-5.1 | $SiN_x$ | 1.4 | 5 | ss 30 b | 1M KCl | N/A |
| [15]FIG. 3 | 3.4 | 400 | 8.5 | $SiN_x$ | 3.4 | 1.5* | ds 3 kbp | 0.9M NaCl | N/A |
| [4]FIG. 2c | 0.5 | 100 | 5 | G | 8 | 1-5 | ds 15 kbp | 1M KCl | N/A |
| [4]FIG. 4c | 1 | 150 | 6.7 | G/$TiO_2$ | 5 × 7 | 1-5/5 | ds 400 bp | 1M KCl | N/A |
| [4]FIG. 5c | 0.2-1.4 | 100-400 | 2.3-3.6 | G/$TiO_2$ | 8 | 1-5/5 | ds 15 kbp | 1M KCl | N/A |
| [5]FIG. 4c | 0.3 | 200 | 1.5 | G | 22 | 0.3 | ds 48 kbp | 1M KCl | N/A |
| [6]FIG. 4 | 1.24 | 160 | 7.8 | G | 4.6* | 0.6* | ds 10 kbp | 3M KCl | N/A |
| [7]FIG. 3a | 4.1 | 160 | 25.6 | G | 2.8 | 0.6* | ds 10 kbp | 3M KCl | 27.5 |
| [9]FIG. 4c | 0.3-0.8 | 100-250 | 3.0-3.4 | $HfO_2$ | 3.6* | 7* | ds 100 bp | 1M KCl | 9.6 |
| [9]FIG. 5b | 0.7-2 | 200-400 | 3.6-4.9 | $HfO_2$ | 1.7* | 2* | ss 89 b | 1M KCl | 9.6 |
| [9]FIG. 5b | 0.6-1.4 | 300-500 | 2.0-2.8 | $HfO_2$ | 1.4* | 4.5* | ss 89 b | 1M KCl | 9.6 |
| [8]FIG. 3c | 1-2 | 100-200 | 9.7-10.2 | BN | 5.4 × 6.4 | 1.3 | ds 10 kbp | 3M KCl | N/A |
| [10]FIG. 3b | 0.3-1.1 | 100-400 | 2.8-3.5 | $MoS_2$ | 20 | 1.6* | p 2.7 kbp | 2M KCl | 20 |
| [10]FIG. 4 | 1 | 200 | 5 | $MoS_2$ | 20 | 1.6* | ds 48 kbp | 2M KCl | 20 |

G: Graphene,
d: diameter,
t: thickness,
σ: conductivity,
Sol: solution and concentration,
b: base,
bp: base pair,
*fitted value.

Figure 2D:
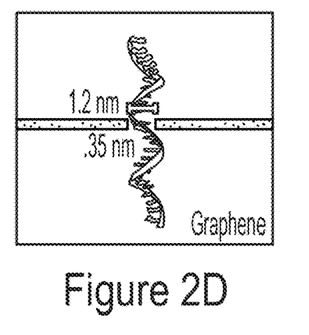

We were able to achieve ~4 nm thin silicon nitride pores ($SiN_x$) with diameters similar to the cross-sectional size of single and/or double stranded DNA, that has the ability to sequence DNA. Since biological nanopores have been used to differentiate individual DNA bases within a specific DNA sequence or as part of homopolymers and show proof-of-principle sequencing, $SiN_x$ nanopores of similar dimensions will produce comparable results. FIGS. 2A-2D show illustrated cross-sections of a 1.2-nm-diameter nanopore in a 5-nm-thick $SiN_x$ membrane (FIG. 2B), alongside cross-sections of α-hemolysin (FIG. 2a) and MspA proteins (FIG. 2c) and graphene (FIG. 2D).

The geometry of nanopores in solid-state membranes drilled using a transmission electron microscope (TEM) is governed by the interplay between surface tension of the molten $SiN_x$ and its ablation kinetics. This geometry can be modified by tuning the electron-beam fabrication process.

showing in comparison how graphene pores have significant issues that still have to be overcome, such as wettability, yield and ease of DNA translocation. There are no fundamental reasons why nanopores have to be exactly one-atom thin, and in fact, even in graphene nanopores, there are theoretical studies indicating that multilayer (thicker) pores may work better. However, it is still very important that nanopores are thin enough (~<1 nm) at their narrowest region, so that only one or a few DNA bases reside in the pore at a given time. $SiN_x$ nanopores have an hourglass shape, making them effectively as thin as ⅓ of the membrane thickness. Our aim is to achieve +/−0.1 nm control over nanopore diameter and thickness and the best tool to achieve this is the scanning transmission electron (STEM) beam.

The thickness of the membrane can be controlled in situ by measuring the current density during the fabrication process in the STEM mode of the TEM. We have programmed the electron beam to drill in the thinnest spots of a small membrane. To do this we control the beam to scan a small area (~20 nm×20 nm) of the $SiN_x$ membrane and etch it during this process. When a desired thickness of the $SiN_x$ is reached, then we drill a pore in the center of that square. FIG. 4 shows thin $SiN_x$ nanopores fabricated in this way, and a resulting height profile of the thinned region (inset). This method yields nanopores of highly controlled size and shape, high reproducibility and wafer-scale scalability.

FIG. 6 shows how the making of pores in the STEM mode in ~40 nm thick $SiN_x$ films depends, for a fixed electron beam diameter D, on the convergence angle α of the beam and the exposure dose (coulombs per square meter). Increasing the convergence angle increases the current density of the beam since more electrons, with a wider angular range, reach the sample. Here, we fixed the beam diameter to D=2.4 nm for three convergence angles (α=58, 33 and 24 mrad; using the convention shown in FIG. 6A), which yielded three current densities (3.8, 0.8, and 0.4×109 A m$^{-2}$, respectively). The convergence angle was controlled by changing the condenser aperture of the Transmission Electron Microscope (TEM). The exposure dose is set and calculated by taking the time that the electron beam lays immobile at the position of the film, where the pore is to be made, and multiplying it by the current density.

We operated the TEM in Scanning TEM (STEM) mode, in which the position of the converged electron beam can be controlled with high spatial precision via automated feedback. In STEM mode, High-Angle Annular Dark Field (HAADF) images, in which the intensities are proportional to the mass, can be routinely acquired.

Figure 6A:
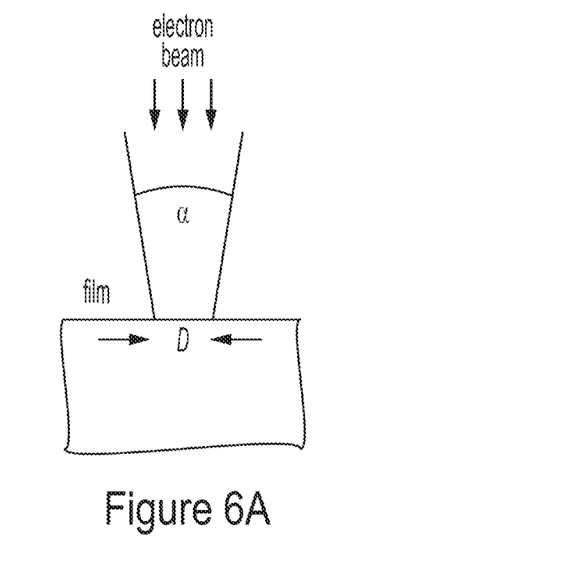
FIG. 6A provides a diagram showing the convergence angle (α) and diameter (D) of the electron beam at the surface of the film facing the electron source.
Figure 6B:
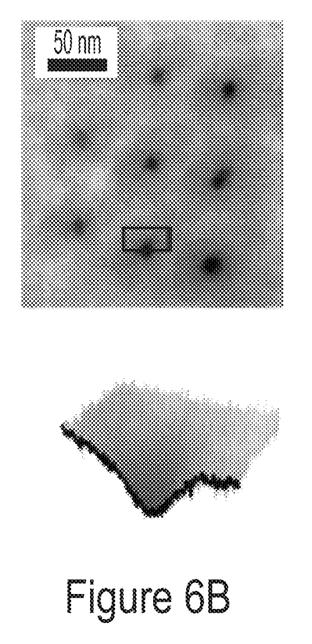
FIGS. 6B-6D, top show HAADF STEM images of a $SiN_x$ film after electron irradiation was carried out with a convergence angle of (A) α=58, (B) 33 and (C) 24 mrad. The intensities of the images are proportional to the film mass, thus darker areas correspond to areas with less mass. The nine spots in each image correspond to nine different exposure doses, attained by increasing the time of irradiation from 10 to 90 seconds, in increments of 10 seconds (from top to bottom and left to right). A perspective view of the intensities of the images enclosed by the highlighted rectangles in FIGS. 6B-6D, top, corresponding to areas of 16×32 nm$^2$, are shown in FIGS. 6B-6D (bottom).
Figure 6C:
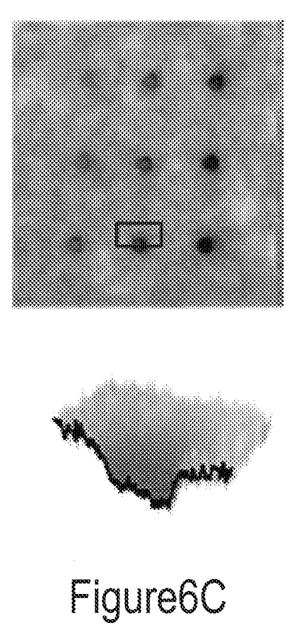
Figure 6D:
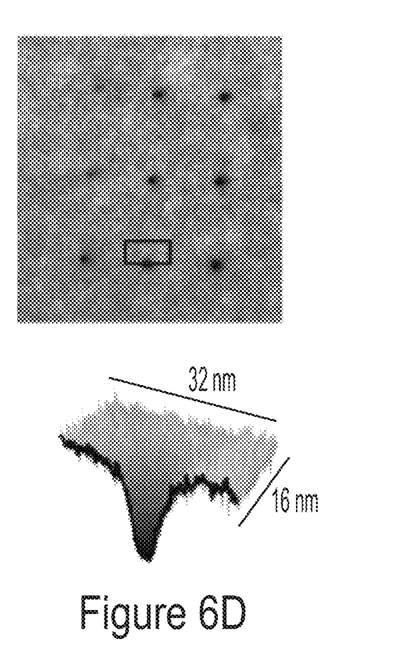

FIGS. 6B-6D show HAADF STEM images obtained from areas of a ~40 nm - - - thick $SiN_x$ film on which nine exposure doses were tested for each convergence angle (α=58, 33 and 24 mrad) by letting the beam immobile in nine different positions, from 10 up to 90 seconds with time increments of 10 seconds between positions. In these images, areas of the $SiN_x$ film with less mass appear darker (considering that the density of the film or the proportion of Si to N did not change during irradiation).

The bottom row of FIGS. 6B-6D show a perspective view of the intensities enclosed by the highlighted rectangles in the HAADF STEM images, corresponding to areas of 16×32 nm2. In these areas the beam rested immobile for 60 seconds in a point, yielding exposure doses of 23, 5 and 2×1010 C m$^{-2}$, for α=58, 33 and 24 mrad, respectively. From these intensity profiles we estimated how much mass (or volume) was lost from the film by irradiation. The shape of the resulting pore can be inferred to some extent, since we know how much mass was lost at each position of the film; however, the exact place where mass was removed in the direction perpendicular to the beam is unknown.

Figure 6E:
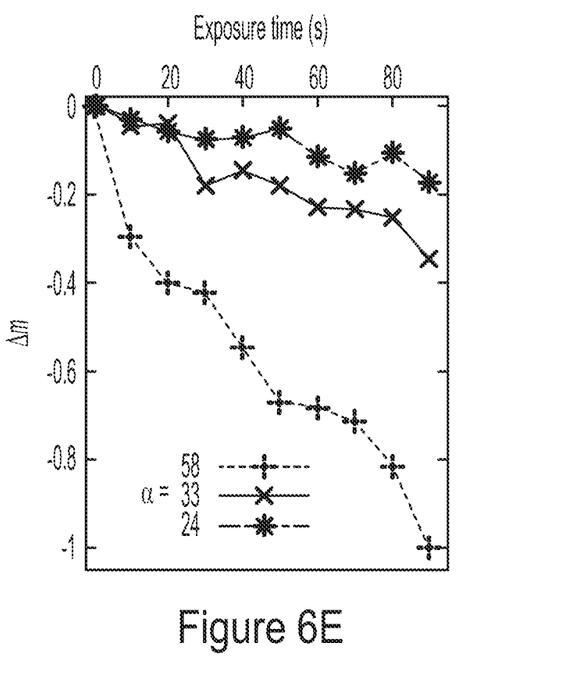
FIG. 6E Normalized total change of mass, $\Delta m$, and FIG. 6F normalized change of mass in the direction parallel to the beam, $\Delta m_z$, of the irradiated areas of the $SiN_x$ film as a function of irradiation time for each convergence angle α: 58 (red), 33 (green) and 24 (blue) mrad.

We calculated the normalized total change of mass, $\Delta m$, of the irradiated areas of the $SiN_x$ film by integrating the intensities in the HAADF STEM images of the irradiated areas, after background subtraction, and dividing the result by the maximum value obtained in all of our measurements (details of this method are provided in the SI); $\Delta m$ is a dimensionless ratio and its values are negative because mass is removed by irradiation. FIG. 6E summarizes these findings, where we plotted $\Delta m$ as a function of exposure time, which is proportional to the exposure dose, for each convergence angle (α=58, 33 and 24 mrad).

FIG. 6E shows that for a fixed current density (a constant) more mass is removed with a higher dose, and for a fixed exposure time more mass is removed with a higher current density. For example, for a current density of 3.8 A m$^{-2}$ (α=58 mrad), 90 seconds of exposure (dose=34×1010 C m$^{-2}$) removed approximately four times the mass removed in 10 seconds of exposure (dose=4×1010 C m$^{-2}$). For the same exposure time, the values of $\Delta m$ scaled closed to the ratio 9:2:1 of the applied current densities. For example, after 60 seconds of irradiation, $\Delta m \approx -0.7$, $-0.2$, and $-0.1$, for current densities of 3.8, 0.8, and 0.4×109 A m$^{-2}$, respectively.

The rate at which mass is removed is larger at the beginning of irradiation, since once a pore is made throughout the film there is no more mass to remove. We emphasis that to make a pore the current density should be larger than a certain threshold, even if the energy of the beam is enough to cause damage to the film.

The depth of the pores is correlated to the mass removed in the direction parallel to the beam, more than to the total mass removed. To quantify this we calculated, for each pore, the normalized change of mass in the direction parallel to the beam, $\Delta m_z$, which was obtained by measuring the difference, in the HAADF STEM images, between the lowest intensity (least mass) found in the center of each pore and the averaged intensity of the unmodified film, after background subtraction. Similar to $\Delta m$, we normalized $\Delta m_z$ by dividing its values by the maximum value obtained in all of our measurements (details of this method are provided in the SI). A whole - - - length pore with a zero film thickness corresponds to a value of $\Delta m_z = -1$.

Figure 6F:
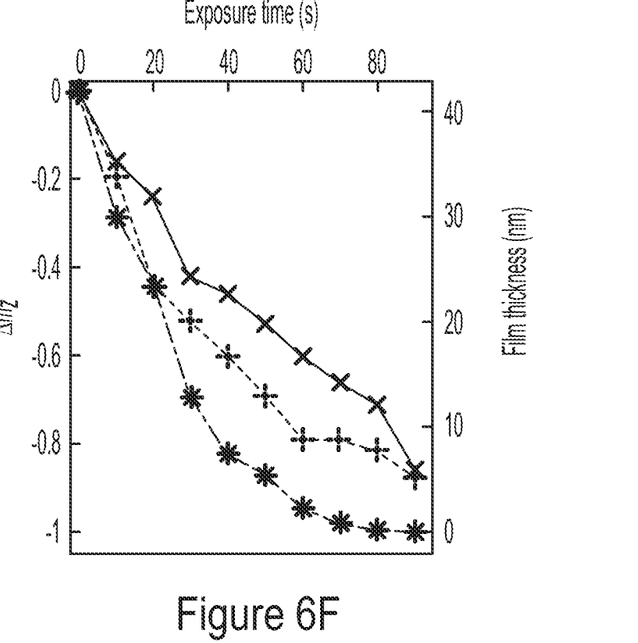
Figure 7A:
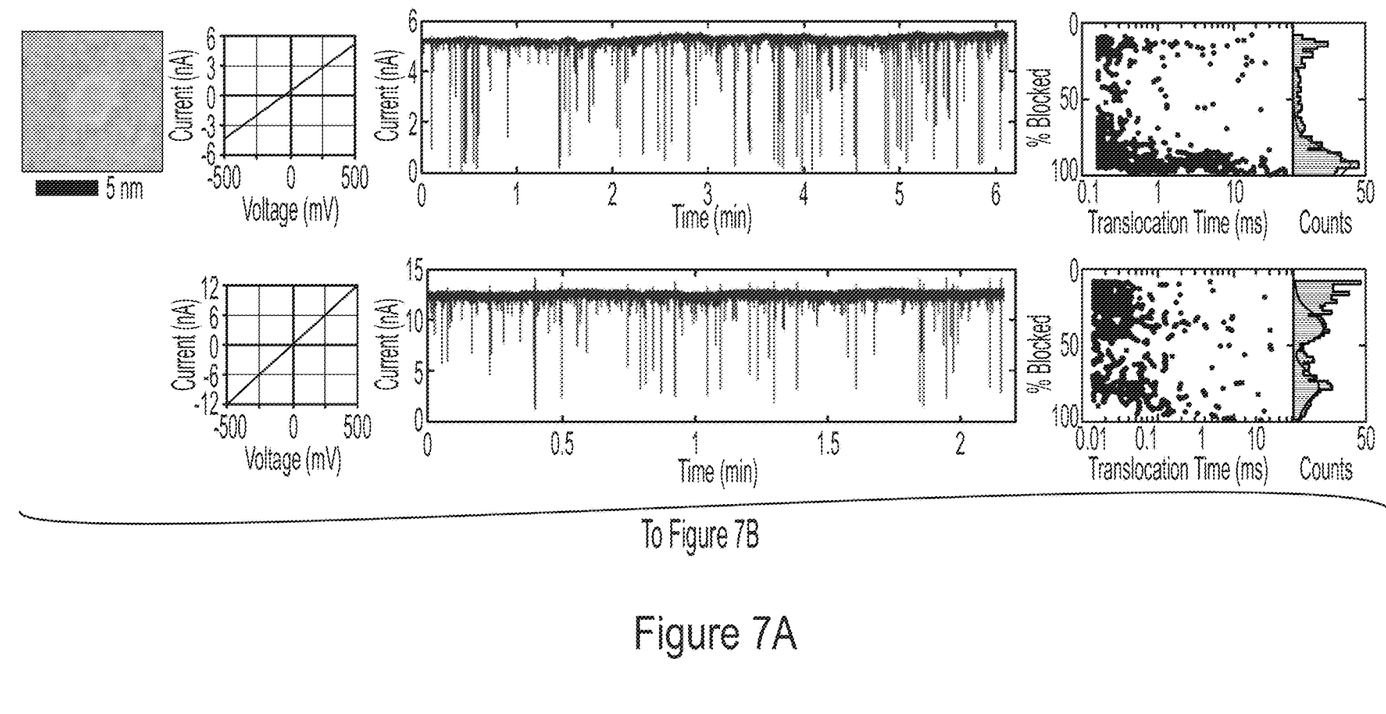
FIGS. 7A-7B provide ionic current measurements of dsDNA translocations through four nanopores fabricated as described in the text. Shown are TEM images, I-V (ion current-voltage curves, ion current vs. time during dsDNA translocations in 1M KCl solution at 500 mV applied, and the corresponding histograms of the percentage of ionic conductance blocked by the DNA molecule ($\Delta G/Go$) vs. translocation time in ms.
Figure 7B:
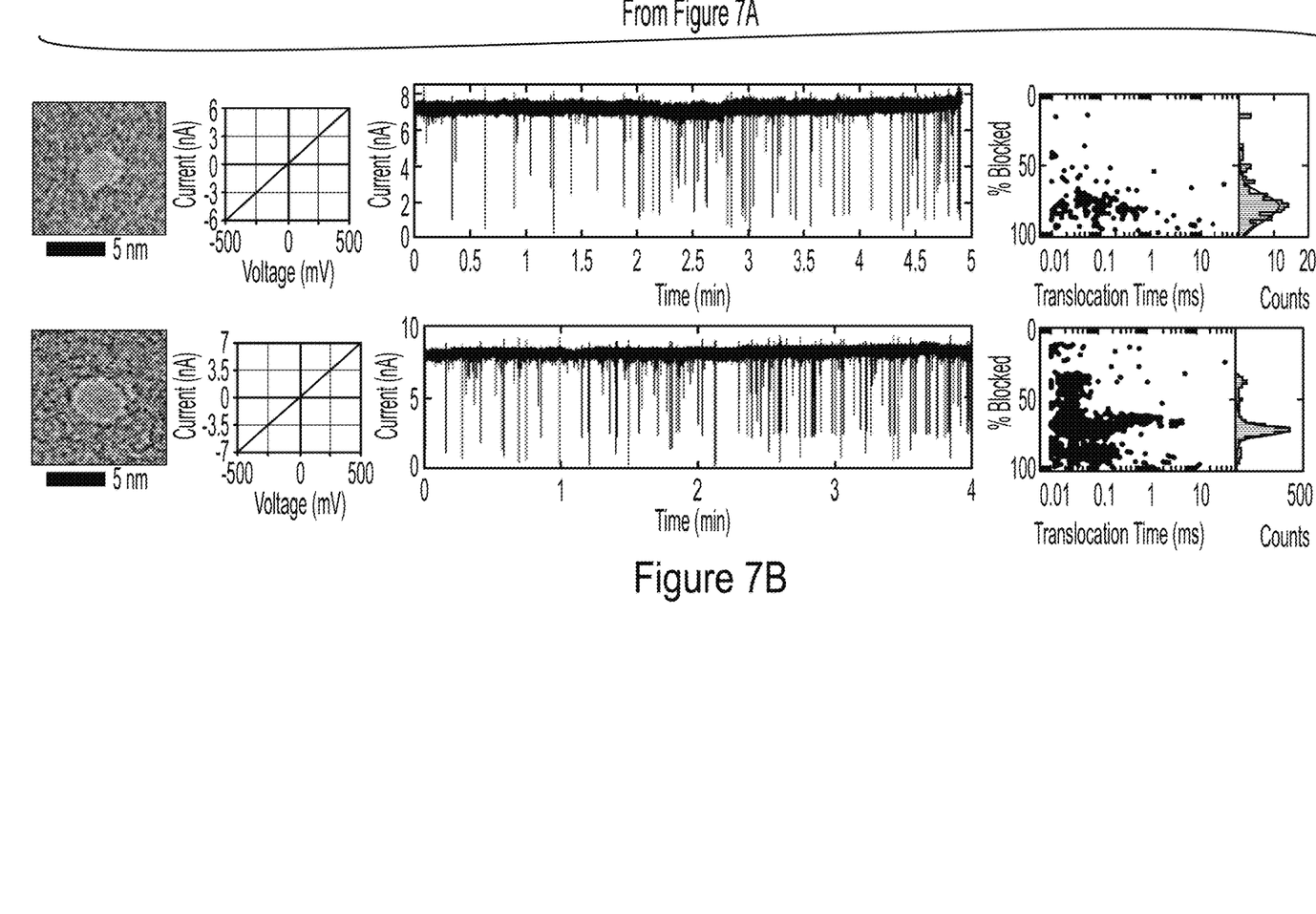

FIG. 6F shows the dependence of $\Delta m_z$ with respect of exposure time for the different beam convergence angles. Within our experimental parameters, for the same exposure time the deepest pores were made consistently with the beam with the smallest convergent angle (α=24 mrad) and, therefore, the lowest current density (0.4×109 A m$^{-2}$). For example, as FIG. 6F shows, for α=24 mrad an exposure dose of 4×1010 C m$^{-2}$ was enough to make a whole-length pore while, for the same exposure time, a dose of 34×1010 C m$^{-2}$ for α=58 mrad was insufficient.

The energy transfer from the beam to the film depends (e.g. elastic collisions) on the angle that the incoming beam makes with the film. Our results indicate that to make small well-defined pores with an electron beam this sometimes neglected parameter must be considered Summarizing, we state that to make a small well-defined pore in the least amount of time, with an electron beam of fix diameter, is better to use a beam with a low convergence angle and, therefore, a smaller exposure dose. Everything else being equal, a beam with a larger convergence angle will remove more mass but in a broader and shallower area.

What is claimed:

1. A method for preparing a nanoporous silicon nitride membrane comprising:
    ablating portions of at least one side of the silicon nitride membrane with an electron beam to give rise to thinned portions such that each thinned portion defines an upper surface parallel to an upper surface of the silicon nitride membrane, each thinned portion having a thickness of between about 0.3 and about 5 nanometers; and
    penetrating the thinned portions of the silicon nitride membrane with an electron beam to form nanopores extending through the thinned portions of the silicon nitride membrane;
    wherein the thinned portions of the silicon nitride membrane are formed essentially of amorphous silicon having therein less than about 10% of the nitrogen present in silicon nitride.

2. The method of claim 1, wherein each of said portions comprises one nanopore.

3. The method of claim 1, wherein the nanopores have an hourglass shape or a cylinder shape.

4. The method of claim 1, wherein the nanopores have a cross-section of less than or equal to about 1 nm at its widest point.

5. The method of claim 1, wherein the nanopores have a cross-section of less than or equal to about 0.5 nm at its widest point.

6. The method of claim 1, wherein the electron beam is a scanning transmission electron beam.

7. The method of claim 6, wherein the thickness of each thinned portion is controlled utilizing measurements of current density.

8. The method of claim 1, wherein each thinned portion is a square or rectangle with each dimension being in the range of about 10-30 nm.

9. The method of claim 1, wherein each thinned portion is 20 nm×20 nm in surface area.

10. The method of claim 1, wherein the nanopores are in the center of each thinned portion.

11. The method of claim 1, wherein the silicon nitride membrane has a thickness in the range of from about 20 nm to about 100 nm prior to contact with the electron beam.

12. The method of claim 1, wherein the thickness of each thinned portion is 2-4 nm.

13. The method of claim 1, wherein the nanopores have a diameter in the range of 1 to ⅓ of the thickness of each thinned portion.

14. A macromolecule analysis component, comprising a nanoporous silicon nitride membrane having an upper surface, the component prepared by a method comprising:
    ablating portions of at least one side of the silicon nitride membrane with an electron beam to give rise to thinned portions such that each thinned portion defines an upper surface parallel to the upper surface of the silicon nitride membrane, each thinned portion having a thickness of between about 0.3 and about 5 nanometers; and
    penetrating the thinned portions of the silicon nitride membrane with an electron beam to form nanopores extending through the thinned portions of the silicon nitride membrane;
    wherein the thinned portions of the silicon nitride membrane are formed essentially of amorphous silicon having therein less than about 10% of the nitrogen present in silicon nitride.

15. The macromolecule analysis component of claim 14, wherein each of said thinned portions comprises one nanopore.

16. The macromolecule analysis component of claim 14, wherein the nanopores have an hourglass shape or a cylinder shape.

17. The macromolecule analysis component of claim 14, wherein the nanopores have a cross-section of less than or equal to about 1 nm at their widest point.

18. The macromolecule analysis component of claim 14, wherein the nanopores have a cross-section of less than or equal to about 0.5 nm at their widest point.

19. The macromolecule analysis component of claim 14, wherein the electron beam is a scanning transmission electron beam.

20. The method of claim 1, wherein discontinuing of the ablating occurs when the N:Si ratio is equal to or less than 0.3.

21. The method of claim 1, wherein discontinuing of the ablating occurs when the N:Si ratio is equal to or less than 0.1.

22. The macromolecule analysis component of claim 14, wherein the silicon nitride membrane is freestanding.

23. A method of sequencing DNA or RNA sequences, comprising:
    with a component that comprises a silicon nitride membrane,
    the silicon nitride membrane comprising (i) a thick region having an upper surface, (ii) a thinned region formed in the thick region, the thinned region having an upper surface, the upper surface of the thick region being parallel to the upper surface of the thinned region,
    the thinned region being formed essentially of amorphous silicon having therein less than about 10% of the nitrogen present in silicon nitride,
    the thinned region having a thickness of from about 0.3 to about 5 nanometers; and
    the thinned region having a nanopore extending therethrough,
    translocating a molecule through the nanopore and detecting a signal related to the translocation of the molecule through the nanopore.

24. The method of claim 23, further comprising contacting a sample to a capture material that preferentially binds to the molecule and eluting the molecule from the capture material.

25. A macromolecule analysis component, comprising:
    a silicon nitride membrane,
    the silicon nitride membrane comprising (i) a thick region having an upper surface, (ii) a thinned region formed in the thick region, the thinned region having an upper surface, the upper surface of the thick region being parallel to the upper surface of the thinned region,
    the thinned region being formed essentially of amorphous silicon having therein less than about 10% of the nitrogen present in silicon nitride,
    the thinned region having a thickness of from about 0.3 to about 5 nanometers; and
    the thinned region having a nanopore extending therethrough.

26. The macromolecule analysis component of claim 25, wherein the nanopore has a diameter of from about ⅓ the thickness of the thinned region to about the thickness of the thinned region.

27. The macromolecule analysis component of claim 25, wherein the nanopore has a diameter of from about 1 nm to about 2.5 nm.

28. The macromolecule analysis component of claim 25, wherein the silicon nitride membrane has a thickness of from about 20 nm to about 100 nm.

29. The macromolecule analysis component of claim 25, wherein the silicon nitride membrane is freestanding.

* * * * *

UNITED STATES PATENT AND TRADEMARK OFFICE
CERTIFICATE OF CORRECTION

| | | |
|---|---|---|
| PATENT NO. | : 11,338,247 B2 | Page 1 of 1 |
| APPLICATION NO. | : 15/511829 | |
| DATED | : May 24, 2022 | |
| INVENTOR(S) | : Marija Drndic et al. | |

It is certified that error appears in the above-identified patent and that said Letters Patent is hereby corrected as shown below:

In the Specification

Under Column No. 4, Line no. 5:
Replace "In FIG. 6F the"
With -- In FIG. 6F, the --

Under Column No. 7, Line no. 51:
Replace "achieve ~4 nm thin"
With -- achieve ~1 nm thin --

Under Column No. 8, Line no. 61:
Replace "as 1/3 of"
With -- as ~1/3 of --

Under Column No. 10, Line no. 44:
Replace "be considered Summarizing,"
With -- be considered. Summarizing, --

Signed and Sealed this
Nineteenth Day of July, 2022

Katherine Kelly Vidal
*Director of the United States Patent and Trademark Office*